United States Patent [19]

Welling

[11] 4,063,410
[45] Dec. 20, 1977

[54] DIGITAL WATCH INCLUDING A SIGNAL TRANSMITTER

[76] Inventor: Gregory J. Welling, 529 N. 33rd St., Omaha, Nebr. 68131

[21] Appl. No.: 662,590

[22] Filed: Mar. 1, 1976

[51] Int. Cl.$^2$ .................. G04C 21/34; G04B 23/12; A61B 5/02; A61B 5/04
[52] U.S. Cl. .................. 58/38 R; 58/57.5; 58/88 R; 58/152 R; 128/2.05 G; 128/2.1 E; 340/279
[58] Field of Search .................. 58/38 R, 57.5, 88 R, 58/152 R; 128/2.05 P, 2.05 G, 2.1 A, 2.1 E; 340/279

[56] References Cited

U.S. PATENT DOCUMENTS

| | | | |
|---|---|---|---|
| 3,032,651 | 5/1962 | Stahli et al. | 58/152 |
| 3,472,019 | 10/1969 | Webb | 58/152 R |
| 3,807,388 | 4/1974 | Orr et al. | 128/2.05 P |
| 3,813,533 | 5/1974 | Cone et al. | 58/152 R |
| 3,937,004 | 2/1976 | Natori et al. | 58/50 R |
| 3,972,320 | 8/1976 | Kalman | 128/2.05 P |

Primary Examiner—E. S. Jackmon
Attorney, Agent, or Firm—Zarley, McKee, Thomte, Voorhees & Sease

[57] ABSTRACT

A digital wristwatch including a transmitter therein for selective activation of a remote electronic circuit by the wearer. The digital wristwatch includes a time-of-day readout encased in a housing supported by a wrist band. Within the watch housing, the following elements are provided: (1) a digital clock circuit for controlling the time-of-day display, (2) a signal transmitter which is operatively, electrically connected to the digital clock circuit, and (3) a battery for operation of both the digital clock circuit and the signal transmitter. The signal transmitter may be activated by one of two methods: (1) a pushbutton switch on the side of the watch housing or (2) by an externally-supplied, electrical signal to terminals on the watch housing. The pushbutton switch extends outwardly from the housing of the watch to enable the wearer to activate the transmitter in a manner which is undetectable to the observer. The terminals, one located under each of the two wristband attachment arms, is used to activate the transmitter from an external device. An example of such an external device would be a pulse rate detector and comparator built into the wristband. The wearer's pulse rate could be monitored and if it exceeded predetermined limits, the signal transmitter would be activated. A receiving station is provided remotely from the wristwatch and is adapted to receive the transmitted signal from the watch to activate an electronic circuit such as a burgler alarm, fire alarm, medical alert, door opener, etc.

3 Claims, 3 Drawing Figures

DIGITAL WATCH INCLUDING A SIGNAL TRANSMITTER

BACKGROUND OF THE INVENTION

This invention relates to a digital wristwatch and more particularly to a digital wristwatch including a signal transmitter provided thereon for activating an electronic circuit positioned remotely from the wristwatch.

The rise in the crime rate makes it desirable to provide some means for alerting the police that a robbery or the like is taking place. It is also desirable to have a means for alerting medical personnel that a grave condition exists with a patient or the like when the patient is unconscious or incapable to sound the alarm. It is also desirable to be able to activate an electronic circuit remotely from the wearer of the watch, i.e. unlock a door, raise a garage door, dial a telephone number, etc.

Therefore, it is the principal object of the invention to provide a digital wristwatch including a signal transmitter provided therein.

A still further object of the invention is to provide a digital wristwatch including a signal transmitter which transmits a signal to a receiving station which in turn activates an electronic circuit.

A further object of the invention is to provide a digital wristwatch which includes a signal transmitter which may be undetectably activated by a switch or by an external device.

A still further object of the invention is to provide a digital wristwatch including a signal transmitter which may activate an alarm, sound an alert, unlock a device, etc.

A still further object of the invention is to provide a digital wristwatch including a signal transmitter which transmits a coded signal.

A still further object of the invention is to provide a digital wristwatch which includes a signal transmitter which is economical to manufacture, durable in use and refined in appearance.

These and other objects will be apparent to those skilled in the art.

BRIEF DESCRIPTION OF THE DRAWINGS

This invention consists in the construction, arrangements and combination of various parts, whereby the objects contemplated are attained as hereinafter more fully set forth, specifically pointed out in the claims, and illustrated in the accompanying drawings, in which:

DESCRIPTION OF THE PREFERRED EMBODIMENT

The digital clock circuit of many digital wristwatches on the market today could be used or adapted to serve as this invention's digital clock circuit. The basic element required by the signal transmitter from the digital clock circuit is the XTAL clock signal. Additional signals would include submultiple clock signals derived from the XTAL clock and used by the time-of-day display. These submultiple clock signals from the digital clock circuit are not critical, however, if available they will reduce the cost and complexity of the signal transmitter. For this discussion, it is assumed the digital clock circuit provides the XTAL clock signal and five submultiple clock signals to the signal transmitter.

The XTAL clock signal provided by the digital clock circuit is the actual carrier signal transmitted by the signal transmitter. Phase-modulated on this carrier signal is a series of pulse codes used by the remote receiver to distinguish between two or more signal transmitters in a given location. By varying the XTAL frequency and changing the arrangement of pulse codes, an unlimited number of different coding combinations can be derived.

Figure 1:
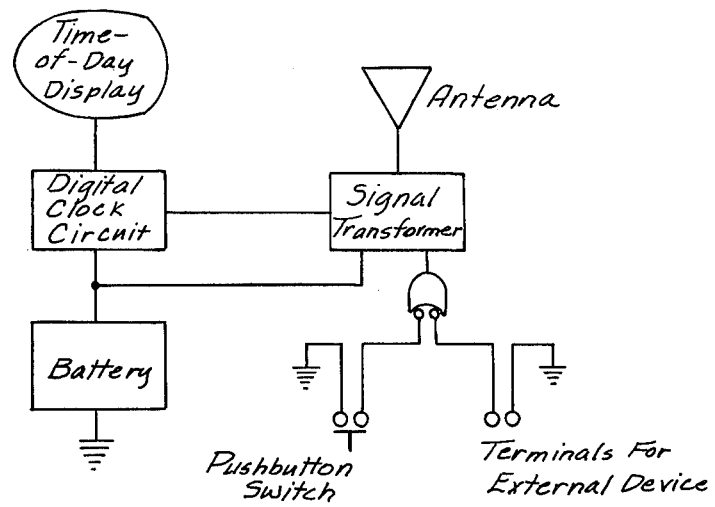
FIG. 1 is a Block Diagram illustrating the Digital Wristwatch including the Signal Transmitter.
Figure 2:
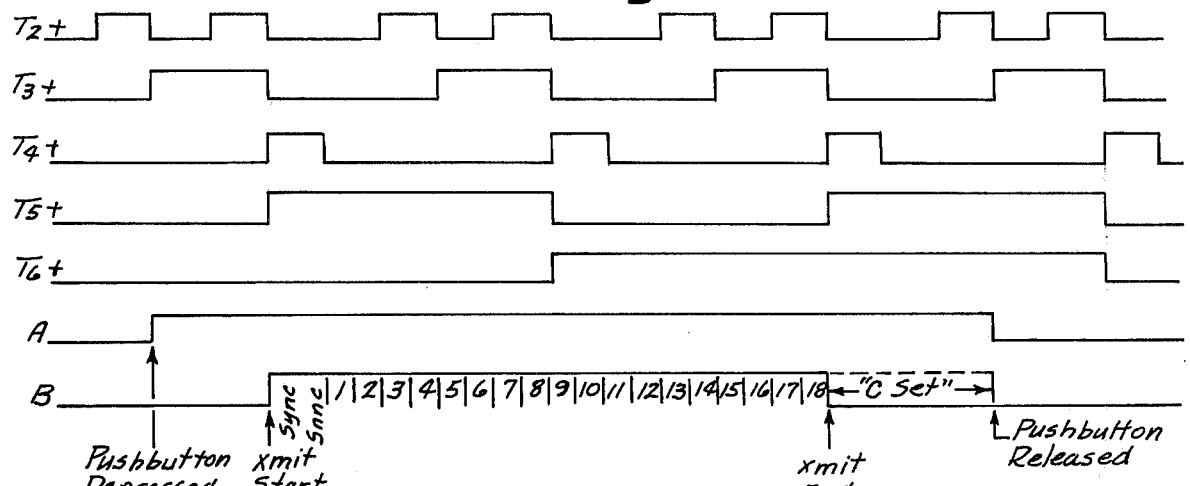
FIGS. 2 and 3 are a logic layout illustrating a typical signal transmitter.
Figure 3:
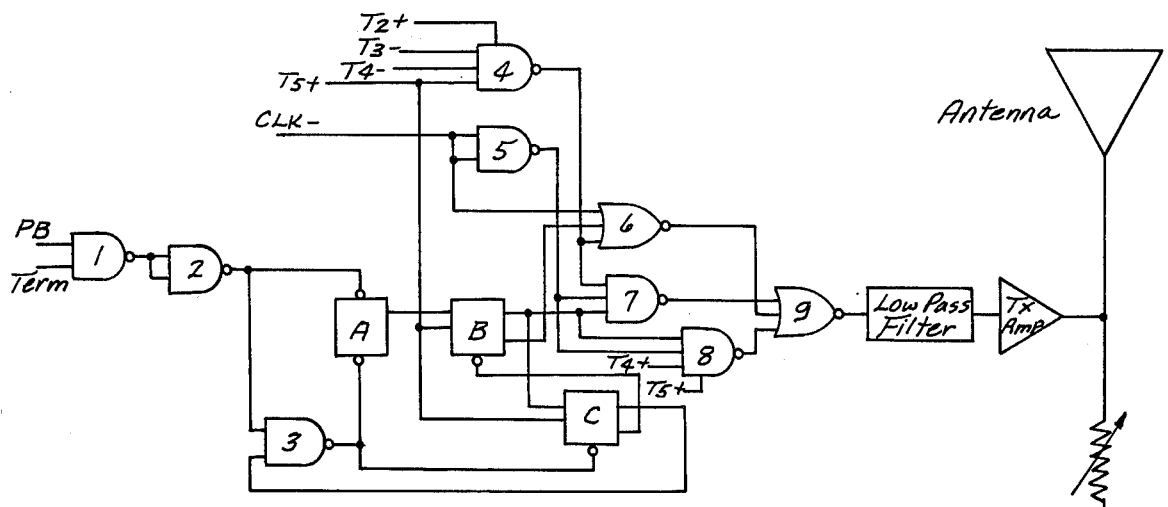

Using the logic layout in FIG. 2 for a brief description of a typical signal transmitter; gate 9 provides one of three carrier signals through a low pass filter, amplified by the transmit amplifier and routed to the antenna for transmission. Gate 8 enables the transmitter to send a synchronizing signal to the receiver during the first two coding periods. Gates 6 and 7 reverse the phase of the carrier according to the coding selected by gate 4. Gates 5 and 2 are inverters. Before actual transmission commences, Flop B must be set to enable gates 6, 7 and 8. By either depressing the Pushbutton (PB) or applying the external TERMinal signal (TERM) through gates 1 and 2 will set Flop A. Flop B will then set at the start of the next available transmit period and remain set until the end of the transmit period. Flop C sets at the end of the transmit period and inhibits further transmissions until the pushbutton is released and pushed again (or the TERM is taken away and re-applied). Gate 3 is used to clear the Flops A and C after the pushbutton is released (or TERM taken away).

For every pushbutton depression (or TERM signal) a coded transmit signal is emitted from the wristwatch. As illustrated in FIG. 2, a possible 18 code elements can be sent during a transmission. This represents a total of 2$^{18}$ or 262,144 different coding combinations for just one XTAL frequency.

I claim:
1. In combination,
   a digital wristwatch including a housing containing a digital circuit for controlling a digital display and a battery for operating said digital circuit,
   a signal transmitter in said housing and being operatively electrically connected to the digital circuit and battery,
   said digital circuit providing a clock signal which is the carrier signal transmitted by said signal transmitter,
   a switch means on said wristwatch for energizing said signal transmitter at times,
   a pair of terminals on said wristwatch for energizing said signal transmitter from an external device at times, and
   said signal transmitter transmitting a coded pulse and frequency signal whereby a remote receiver may distinguish between a plurality of different signal transmitters in a given location.

2. The combination of claim 1 wherein said switch means comprises a stem extending outwardly from said housing.

3. The combination of claim 1 wherein said transmitter includes an antenna extending around the digital display.

* * * * *